United States Patent [19]
Davis

[11] Patent Number: 5,762,634
[45] Date of Patent: Jun. 9, 1998

[54] PROTRACTABLE AND RETRACTABLE HYPODERMIC NEEDLE SYRINGE

[75] Inventor: Melvin Davis, Decatur, Ga.

[73] Assignee: Vista Medical Innovations, Inc., Atlanta, Ga.

[21] Appl. No.: 514,951

[22] Filed: Aug. 14, 1995

[51] Int. Cl.⁶ .................................................. A61M 5/32
[52] U.S. Cl. .......................................... 604/195; 604/263
[58] Field of Search .............................. 604/110, 263, 604/192, 195, 198, 187, 218

[56] References Cited

U.S. PATENT DOCUMENTS

| | | |
|---|---|---|
| 5,188,599 | 2/1993 | Botich et al. |
| 5,195,985 | 3/1993 | Hall ........................... 604/195 |
| 5,222,945 | 6/1993 | Basnight . |
| 5,342,308 | 8/1994 | Boschetti . |
| 5,346,480 | 9/1994 | Hess et al. |
| 5,393,301 | 2/1995 | Goldberg ..................... 604/263 X |
| 5,401,249 | 3/1995 | Shields ........................ 604/195 X |

OTHER PUBLICATIONS

Brochure by US Medical Insutrments, Inc. © 1994.
Plastics World, Aug. 1993, vol. 51, No. 8, pp. 5, 14, 20–24.

Primary Examiner—John D. Yasko
Attorney, Agent, or Firm—Needle & Rosenberg, P.C.

[57] ABSTRACT

A protractable and retractable hypodermic needle syringe device having a syringe barrel, a cylindrical plunger with a cam sleeve, a cam drive shaft, a needle carrier with a cam follower tab, and a hypodermic needle. The hypodermic needle can be moved by the cam system from a retracted position within the plunger to a protracted, operable position. The needle can be detached in the operable position, and reattached after use, onto the needle carrier. The plunger has a resealable membrane which is traversed by the needle and can be selectively prevented from longitudinal movement within the syringe barrel.

13 Claims, 7 Drawing Sheets

PROTRACTABLE AND RETRACTABLE HYPODERMIC NEEDLE SYRINGE

BACKGROUND OF THE INVENTION

1. Field of the Invention

The present invention relates to the field of hypodermic needle syringes and more particularly, to a hypodermic syringe wherein the hypodermic needle may be protracted or retracted into the syringe plunger.

2. Background of the Prior Art

Various types of hypodermic needles currently exist in the art, with the object being to provide a protective cap, cover, or sheath to shield the needle prior to, or after use. Syringes are often used for administering medication to patients suffering from infectious diseases. Numerous cases have been reported in which doctors, nurses, or other medical personnel have been infected by accidental needle sticks. The seriousness of the problem has become more acute in light of the recent spread of Acquired Immunodeficiency Syndrome (AIDS). Accordingly, it is of the utmost importance that extreme care be exercised in the handling and disposal of hypodermic syringes used to prevent the accidental transmission of the HIV virus, as well as other infectious diseases.

Most prior art hypodermic syringes have a cap-like shield mounted over the syringe. The shield protects the needle from damage and contamination, as well as protects the user from accidental needle sticks. The cap-like shield is removed and sometimes discarded when the hypodermic syringe is about to be used.

Accidental needle sticks that occur after the needle has been used generally pose a greater health risk. To avoid such accidents, many prior art hypodermic syringes include a rigid cylindrical safety shield telescoped over the syringe barrel. The prior art safety shield or sheath can be slid or telescoped by spring assist from a proximal position where the needle is exposed for use, to a distal position where the safety shield or sheath protectively surrounds the needle. The prior art also discloses hypodermic syringes that retract the injection needle within the syringe barrel and plunger.

The prior art protective shields and retractable devices are generally suitable for protecting medical personnel from accidental needle sticks and satisfy many of the functional requirements of safety syringes. However, these prior art devices suffer from several drawbacks. One drawback is the complexity of the devices. Many of the prior art devices have complicated structures with multiple parts. The complexity of these devices also have a negative impact on manufacturability, which makes them relatively costly to produce. The high cost to produce these devices adversely affects economic efficiency and integration of the prior art devices within the medical community. Most prior art devices are limited in their size selection and the awkwardness in using the device. Another disadvantage is related to bulk disposal of such high priced, elaborately designed prior art devices.

It is desirable that the hypodermic injection needle be made available in a safe condition prior to injection so as to prevent accidental needle sticks. It is also a requirement that after injection, the needle can be safely and easily discarded without representing a continued health risk to anyone who may encounter the hypodermic syringe, either on the premises of the health care facility, or in transit or arrival at the refuse collection area.

There is a great interest in the health care industry to manufacture, sell, distribute and use a hypodermic syringe that provides the type of safety described above. There is a need for a reliable device that instills confidence in the user, provides simple operation, and an inexpensive means to manufacture. Such a device should have a great deal of versatility for various fields of application such as medical, laboratory, dentistry, veterinary and industrial. It should also provide a broad range of syringe sizes, along with the capability to protract-retract needles from ½" inch to 6" inches in length.

The features described above as being desirable for hypodermic syringes are all provided for by the present invention. Other features of the invention will be pointed out or will occur to those skilled in the art from a reading of the following specification, in conjunction with the accompanying drawings, which show for illustrative purposes only, a preferred form of the invention.

OBJECTS OF THE INVENTION

Therefore, it is a object of the present invention to provide a hypodermic syringe system of the character indicated as desired in the art.

A specific object is to provide a hypodermic injection system utilizing co-acting cams and a cam follower for the purpose of selective protraction and retraction of a injection needle.

Another object of the invention is to provide automatic transfer of the injection needle from the interior proximal end of the plunger to the exterior distal end of the plunger in the course of relative clockwise rotation from a control knob to the proximal end of the plunger.

A further object of the invention is to provide that once transfer has been effected to the distal end of the syringe plunger, the protract-retract action of the plunger shall be smooth and continuous over the full longitudinal range of stroke.

It is a further object to utilize a resealable membrane on the plunger that is constructed of a flexible material with elastic memory tendencies for self sealing characteristics after actual penetration by the forward end of the needle.

A further specific object is to provide a means to retain the injection needle to the interior distal end of the dosage barrel to complete protraction, whereby relative rotation of the locking control at the proximal end of the syringe co-acts with grooves on the exterior proximal end of the plunger.

Another specific object is to selectively permit the plunger to move longitudinally within the syringe barrel, providing the traditional method of fluid dosage draw and dispensing it thereafter with the plunger.

It is also a specific object to provide a syringe that fully retracts the injection needle back within the interior cavity of the syringe plunger, thus isolating the needle in it's own sharps container.

Further general objects of the invention are to:

(a) Eliminate the use of an excessive number of parts, such as springs, snaps and detents, and elaborate bulk disposal designs, which complicate manufacturing.

(b) Provide a safety syringe with a innovative design encompassing quality, inexpensive cost to manufacture, safety, and simplicity.

(c) Provide a device that gains the acceptance of its users.

Other objects and various further features of novelty and invention will be pointed out or will occur to those skilled in the art from a reading of the following specification, in conjunction with the accompanying drawings, which show, for illustrative purposes only, preferred forms of the invention.

SUMMARY OF THE INVENTION

The present invention provides a protractable and retractable hypodermic needle syringe device comprising a syringe barrel, a cylindrical plunger with a cam sleeve, a cam drive shaft, a needle carrier with a cam follower tab, and a hypodermic needle. The hypodermic needle can be moved by the cam system from a retracted position within the plunger to a protracted, operable position. The needle can be detached in the operable position, and reattached after use, onto the needle carrier. The plunger has a resealable membrane which is traversed by the needle and can be selectively prevented from longitudinal movement within the syringe barrel.

DETAILED DESCRIPTION OF THE INVENTION

Figure 2:
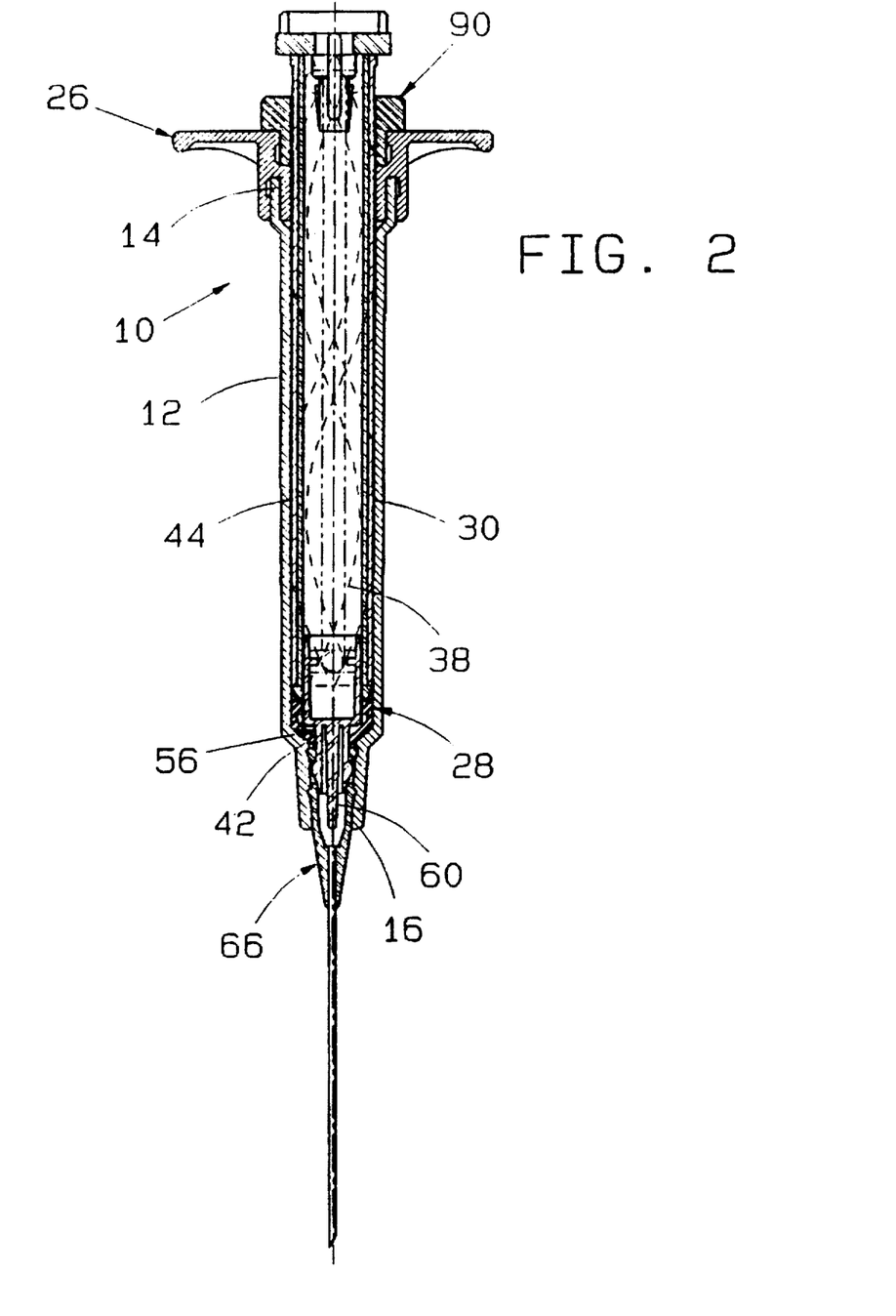
FIG. 2 is a cross-sectional view along the longitudinal direction of the invention in the protracted and operable position.
Figure 3:
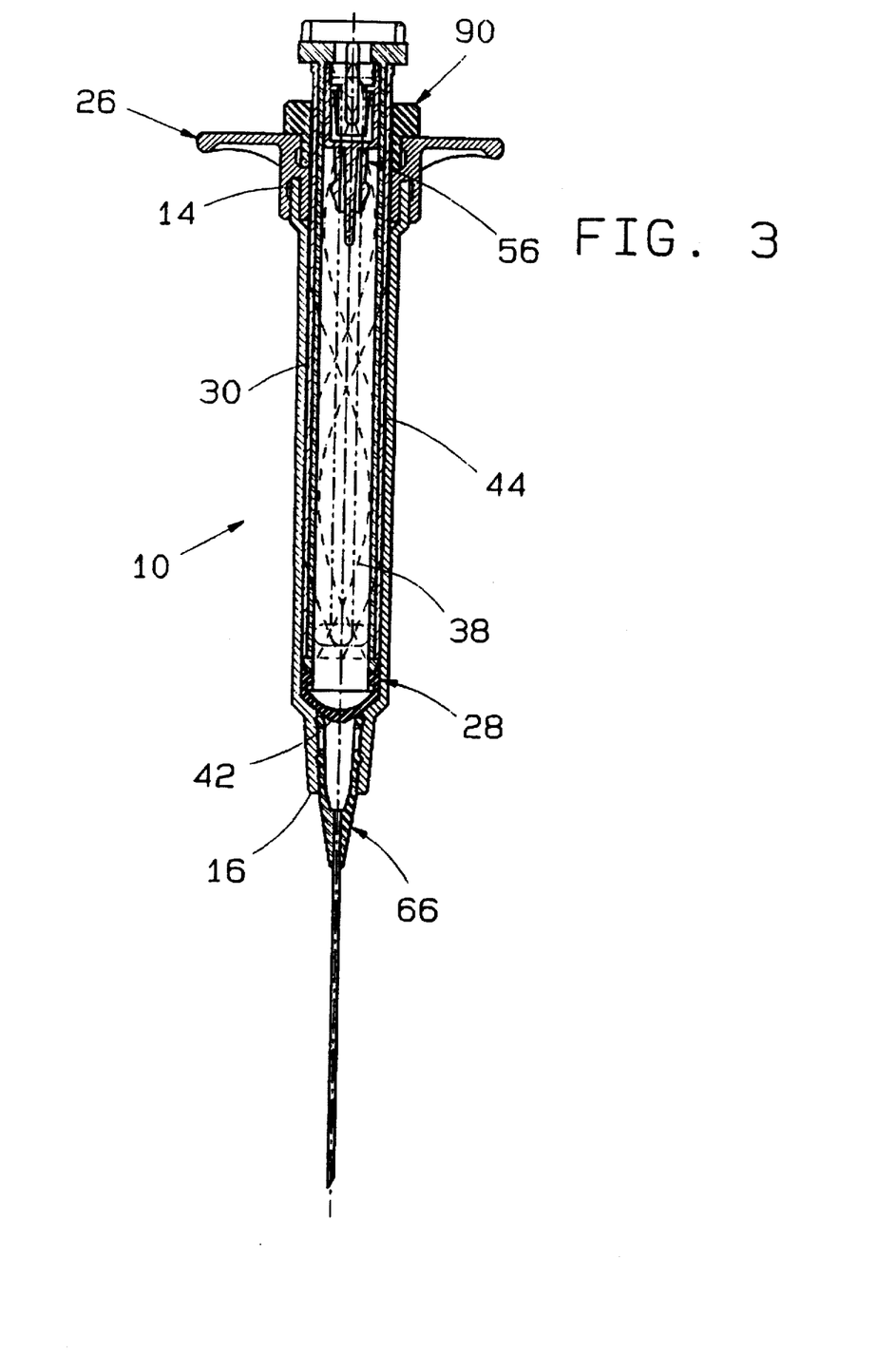
FIG. 3 is a cross-sectional view along the longitudinal direction of the invention with the needle carrier in the retracted position.
Figure 4:
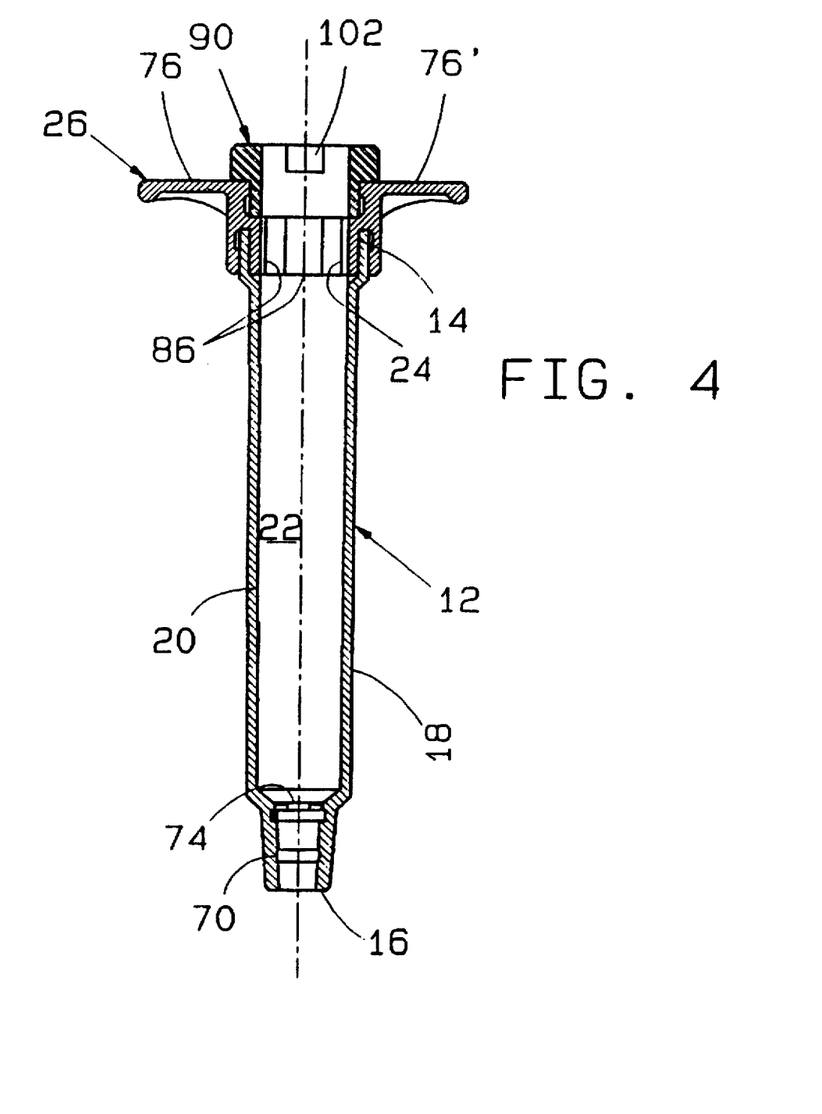
FIG. 4 is a cross-sectional view along the longitudinal direction of the syringe barrel of the present invention.

As shown in FIGS. 1–4, the present invention provides a protractable and retractable hypodermic needle syringe device 10 comprising a syringe barrel 12 having a proximal end 14, a distal end 16, an outside surface 18, and an inside surface 20 defining a dosage chamber 22 and having a key 24 laterally projecting from the inside surface 20 into the dosage chamber 22. As used herein, "a" means one or more than one, depending upon the context within which it is used. For example, FIG. 4 shows that a plurality of keys 24 can be located on a finger control 26 on the inside surface 20.

Figure 5:
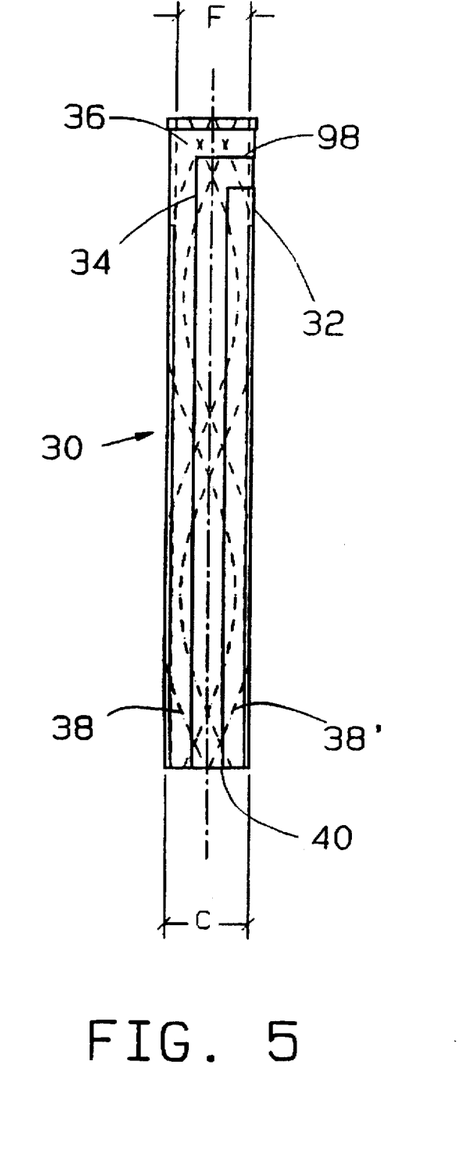
FIG. 5 is a side view of the cam sleeve of the present invention.

A cylindrical plunger 28 is adapted for selective linear longitudinal movement within the syringe barrel 12 between a dosage loading position wherein the plunger 28 is moved toward the proximal end 14 of the syringe barrel 12 and a dosage discharging position wherein the plunger 28 is moved toward the distal end 16 of the syringe barrel 12. Referring specifically to FIG. 5, the plunger 28 has a cam sleeve 30 having an outside surface 32 (diameter "c") defining a groove 34 longitudinally extending along a portion of the sleeve 30 and being complimentarily shaped to, and in registry with, the key 24 (FIG. 4), and an inside surface 36 (diameter "F") having a helical cam groove 38 longitudinally extending therealong. More preferably, the elements of the cam system are provided in duplicate, to create diametrically opposed forces, such that a pair of helical cam grooves 38, 38' are provided.

The plunger 28 has a proximal end 39, a distal end 40, and a resealable membrane 42 positioned over the distal end 40. The resealable membrane 42 can be formed of a butyl rubber material known to those experienced in the art for its self sealing characteristics.

Figure 6:
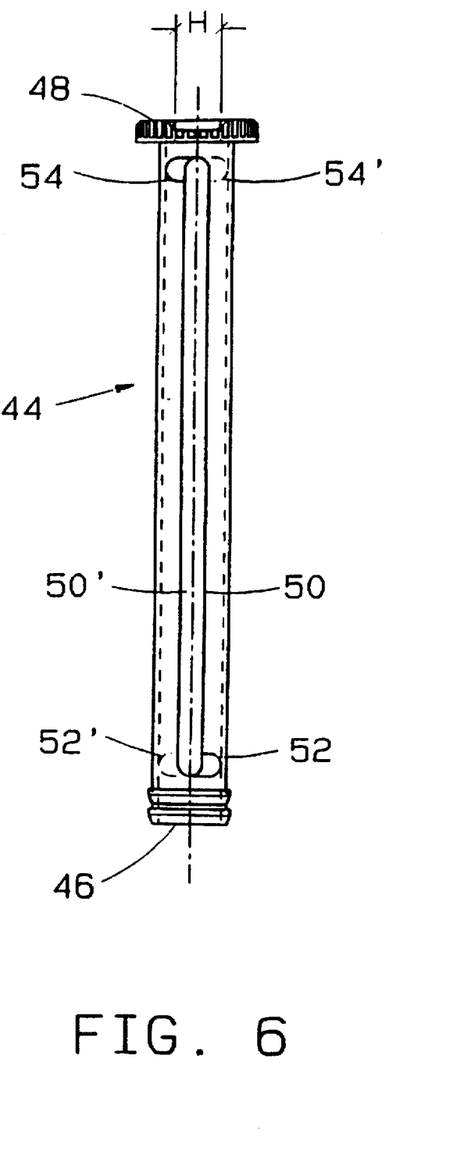
FIG. 6 is a side view of the cam drive shaft of the present invention.

Referring to FIG. 6, a cylindrical cam drive shaft 44 is rotatable positioned within the cam sleeve 30, having a forward end 46, a rear end 48, and a longitudinal cam slot 50 therethrough. The cam drive shaft 44 can be adapted with a longitudinal cam slot 50 having opposed ends 52, 54 that laterally terminate in oppositely directed stop slots.

Figure 7:
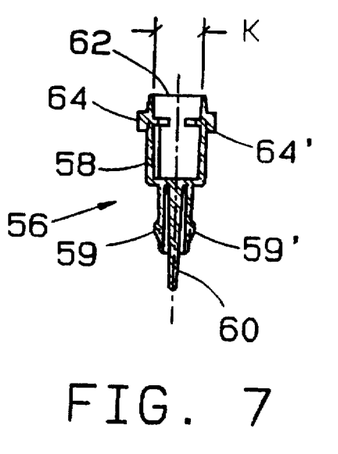
FIG. 7 is a cross-sectional view along the longitudinal direction of the needle carrier of the present invention.

FIG. 7 shows a needle carrier 56 which can be movably positioned within the cam drive shaft 44 comprising a body portion 58 having a forward end 60, an opposite rear end 62, and a cam follower tab 64 laterally projecting from the body portion 58 in communication with both the longitudinal cam slot 50 on the cam drive shaft 44 and the helical groove 38 on the cylindrical cam sleeve 30. The carrier 56 is movable between a protracted position toward the distal end 16 of the syringe barrel 12, and a retracted position toward the proximal end 14 of the syringe barrel 12. In preferred embodiments, a pair of cam follower tabs 64, 64' are provided to communicate with both of the longitudinal cam slots 50, 50' and helical grooves 38, 38'.

Figure 8:
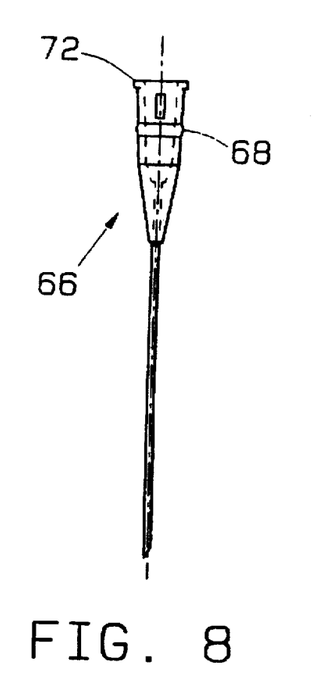
FIG. 8 is a side view of the hypodermic needle of the present invention.

FIG. 8 shows a hypodermic needle 66 which can be detachably mounted on the forward end 60 of the body portion 58 of the needle carrier 56. Rotating the cam drive shaft 44 in a first direction engages the cam follower tab 64 and rotates the needle carrier 56 to its protracted position via the helical groove 38, resulting in the needle 66 penetrating the resealable membrane 42 and moving to its operable position. Rotating the cam drive shaft 44 in an opposite second direction engages the cam tab 64 and rotates the needle carrier 56 to its retracted position.

As shown in FIGS. 1–4 and 8, a sealing means can be provided between the needle 66 and the syringe barrel 12 when in the operable position. The sealing means comprises an annular rib 68 extending circumferentially about the needle 66 and an annular indentation 70 on the distal end 16 of the interior surface 20 of the syringe barrel 12 in mating engagement with the rib 68 when in the operable position. The distal end 16 of the interior surface 20 of the syringe barrel 12 and the rib 68 may be adapted with colored foil or other indicator means to confirm sealing and warn its users that the needle is in the operable position.

In another preferred embodiment shown in FIGS. 4 and 8, the invention provides a means for selectively retaining the needle 66 in the operable position. The retaining means can be a locking tab 72 extending from the needle 66 in rotatable communication when in the operable position with a corresponding notch 74 on the interior of the distal end 16 of the syringe barrel 12, thereby locking the needle 66 in the protracted position. This retaining means can be of the type commonly known as a Luer lock.

Figure 1:
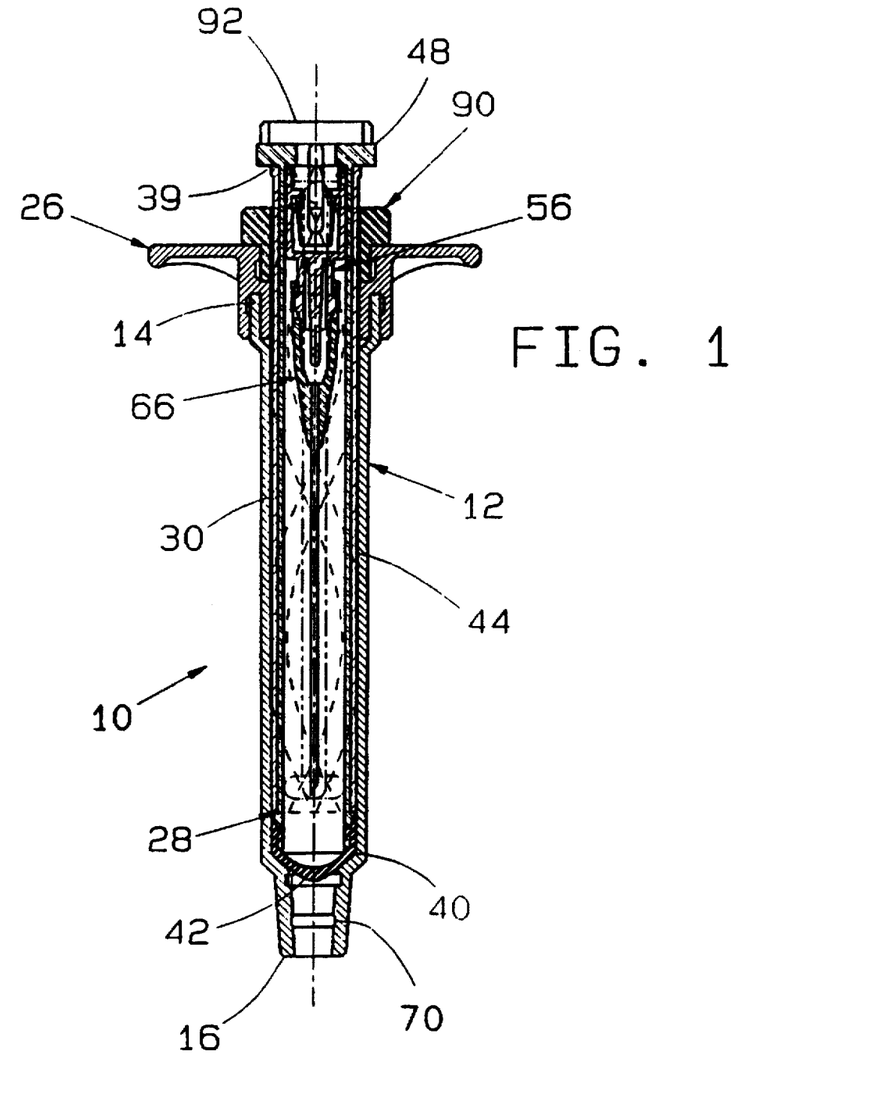
FIG. 1 is a cross-sectional view along the longitudinal direction of the hypodermic needle syringe system of the present invention in the retracted position.

FIGS. 1–3 show a finger support 26 adjacent the proximal end 16 of the syringe barrel 12 comprising a pair of laterally extending finger flanges 76, 76' providing a position for engagement by the index finger and middle finger of the user (not shown) while moving the plunger 28 into the dosage discharging position.

The invention also provides a means for selectively releasing the needle 66 when in the operable position. FIGS. 1–4, 9 and 10 show that the releasing means can be a finger control knob 26 positioned adjacent the proximal end 14 of the syringe barrel 12. The knob has a cylindrical body portion 80 extending about the proximal end 14 of the syringe barrel 12, and a key 24 laterally extending from the inside surface corresponding to, and in rotatable communication with, the longitudinal groove 34 on the cam sleeve 30. The needle carrier 56 is thus movable between a release position wherein the forward end 60 of the needle carrier 56 releases the needle 66 in the operative position, and a retaining position wherein the forward end 60 of the needle carrier 56 retains the needle 66. Retraction of the needle 66 causes coupling snaps 59, 59' (FIG. 7) to deflect, freeing the needle carrier 56 from the locked needle 66.

Figure 9:
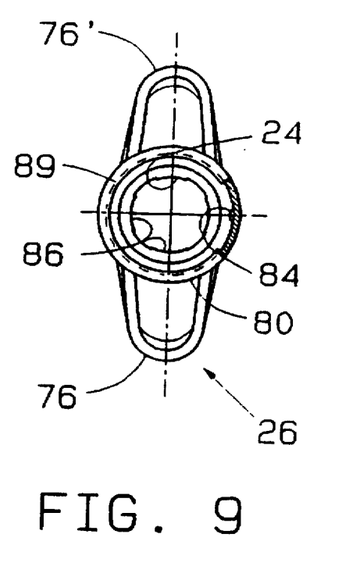
FIG. 9 is a distal view of the finger control of the present invention.
Figure 10:
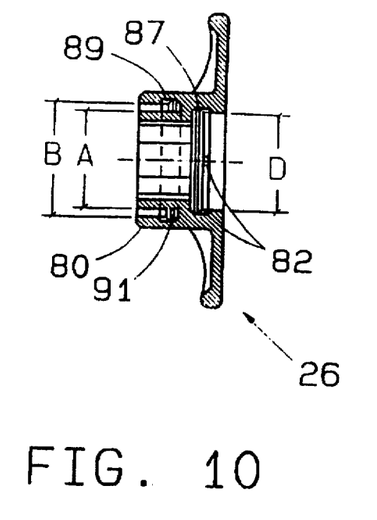
FIG. 10 is a cross-sectional view along the longitudinal direction of the finger control of the present invention.
Figure 11:
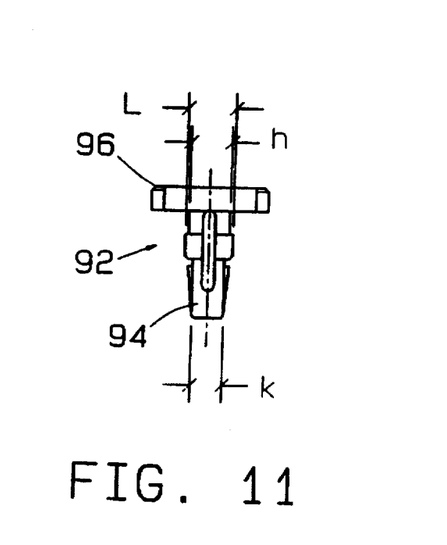
FIG. 11 is a side view of the plug of the present invention.
Figure 14:
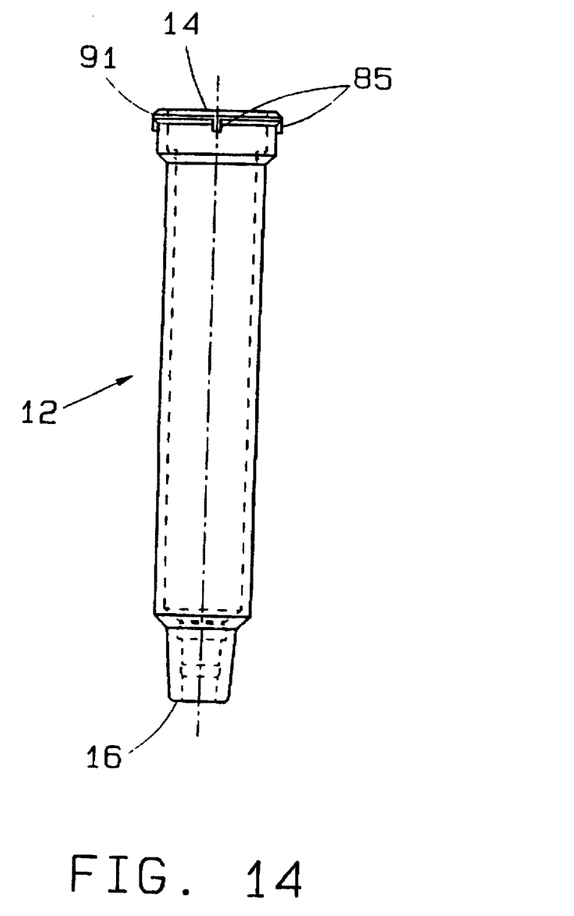
FIG. 14 is a side view of the syringe barrel of the present invention with the inside surface shown in phantom lines.

The finger control knob 26 can also have an outer coupling sleeve 80, which includes a inner circumferential surface diameter "B" characterized by an annular groove 89 dimensioned and disposed to be engaged by an annular snap protrusion 91 located on the proximal end 14 of the syringe barrel 12, as show in FIG. 10. More particularly, four stop ribs 84 (FIG. 9) junctioned between inner surface diameter "B"and annular groove 89 provide a means for relative rotational indexing of 90 degrees with a positive stop against the stop points 85 on the annular protrusion 91 (FIG. 14). Therefore, the finger control 26 is joined and retained frictionally by the annular snap protrusion 91.

Figures 12, 13:
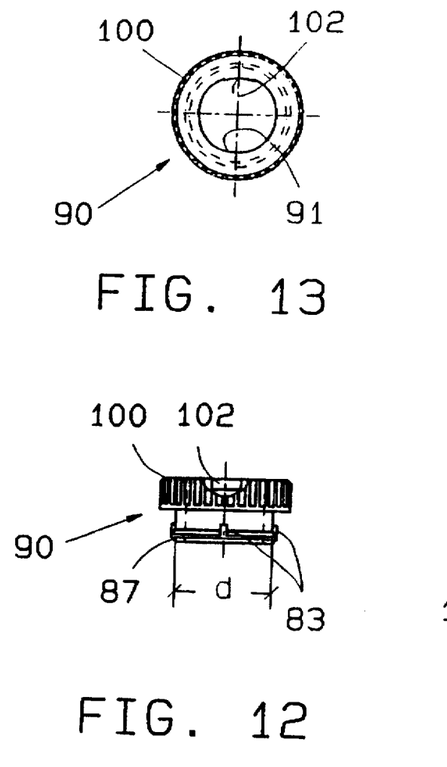
FIG. 12 is a side view of the plunger control knob of the present invention.
FIG. 13 is a cross-sectional view along the longitudinal direction of the plunger control knob of the present invention.

As seen in FIGS. 9 and 10, the finger control 26 further defines a concentric inner surface of diameter "A" having an inner circumferential array of splined teeth 86 and a key 24. The inner splined teeth 86 are engageable with the longitudinal groove 34 of the plunger's helix cam sleeve 30. The finger control knob 26 identifies an opening "D" that houses a second annular snap protrusion 87 within a second grove 82. More particularly, as shown in FIG. 12, the annular protrusion 87 also has four stop points 83. The annular protrusion 87 is dimensioned and disposed as a means for coupling a plunger control knob 90, described below, to the finger control knob 26 thereby, being retained and rotatable allowing indexing with a positive stop.

The invention also provides a means for selectively locking the needle carrier 56 in the retracted position. FIGS. 1–3, 6, 7 and 11 show that the locking means can comprise the rear end 62 of the needle carrier 56 defining an opening "K" into the body portion 58 (FIG. 7) and a carrier lock plug 92 (FIG. 11) having a forward portion 94, width "k", which is detachably mounted in the opening K. The locking means further comprises the carrier lock plug 92 having a rear portion 96 which extends through the rear end 48 of the drive shaft 44, and having a diameter "h" which is greater that the diameter "H" (FIG. 6) of the drive shaft 44 when in a selected locked position. The rear portion 96 is rotatable between a locked position wherein the forward portion 94 of the plug 92 retains the needle carrier 56 in the retracted position, and an unlocked position wherein the forward portion 94 of the plug 92 releases the needle carrier 56.

Furthermore, the invention provides a means for selectively preventing the plunger 28 from longitudinal movement. As shown in FIGS. 1–3, 5, 12 and 13, the preventing means can be a groove 98 radially extending from the longitudinally extending groove 34 on the cam sleeve 30 and being located adjacent the proximal end 39 of the cam sleeve 30. A plunger control knob 90 is located adjacent and external to the proximal end 14 of the syringe barrel 12 and a key 102 laterally extends from the inside surface 91. The key 102 is rotatable between a locked position wherein the key 102 is in engagement with the radial groove 98 and out of registry with the longitudinal groove 34 on the outside surface 32 of the cam sleeve 30 preventing the plunger 28 from moving longitudinally within the syringe barrel 12, and an unlocked position wherein the key 102 is in engagement with the longitudinal groove 34 and out of registry with the radial groove 98, thereby permitting the plunger 28 to move longitudinally within the syringe barrel 12.

The design of the present invention lends itself to different size syringes, and the number of revolutions of the cam drive shaft 44 will be correspondingly affected in order to produce hypodermic syringes having different barrel 12 and plunger 28 sizes, as well as injection needles 66 ranging from, for example, ½ inch to 6 inches. It is contemplated by the invention that other medical devices which present a risk of injury via sharp points or edges can utilize a cam drive shaft and cam follower to protract and retract the offending point or edge within the body of the device. Specific examples include, but are not limited to, intravenous connectors, intravenous indwelling catheters, phlebotomy adapters, scalpels, butterfly catheters and the like.

OPERATION OF THE PREFERRED EMBODIMENT

The present invention provides hypodermic needle syringe device 10 that is entirely safe prior to and after use. The invention provides in combination a protractable-retractable injection needle 66 and an accident proof isolation container that may be discarded after use, preventing needle 66 stick injury or the transmission of diseases by blood borne pathogens. In addition, the hypodermic syringe of the present invention is inexpensive and easy to manufacture, easy to use, and provides visual and tactile confirmation that the needle 66 has been protracted, or safely retracted after use.

Having thus described the present invention, the elements combined are capable of establishing the following sequence of operating events:

(a) The first step is to protract the injection needle carrier 56 so as to move the needle 66 to the operable position. The plug 92 is turned 90 degrees counter-clockwise to free the needle carrier 56 for movement. The needle carrier 56 is protracted by one 360 degree clockwise rotation of the cam drive shaft 44. Hence, movement of the cam drive shaft 44, relative to the cam sleeve 30, brings the edges of slots 50, 50' and the edges of helical grooves 38, 38' into longitudinally driving relation with their associated cam tabs 64, 64', resulting in projecting advancement of the injection needle 66 and carrier 56.

(b) With continued clockwise rotation of the drive shaft 44, the advancement of the injection needle 66 and carrier 56 reaches a maximum point of penetrating and traversing the piston membrane 42. Longitudinal advance beyond this point is precluded by the finite proximal end 39 of the cam sleeve 30. Clockwise rotation of the drive shaft 44 moves the injection needle 66 and carrier 56 to the maximum advancement point, until all such clockwise rotation is terminated by the abutment of cam tabs 64, 64' with radial offsets 52, 52'. The cam drive shaft 44 positions the injection needle 66 into the operable position within the syringe barrel 12 in a frictionally fitted pressure-tight seal.

(c) Thereafter, the finger control knob 26 is rotated 90 degrees in a clockwise direction, to co-act with the plunger's cam drive shaft 44 and needle carrier 56 to index the fully protracted injection needle 66 into a locked position. The needle 66 can be thereafter separated from the carrier 56 by rotating the drive shaft 44 in the counter-clockwise direction, causing the coupling snaps 59, 59' to deflect, freeing the carrier 56 from the now locked injection needle 66.

(d) Retraction of the carrier 56 for storage proceeds from subsequent counter-clockwise relative rotation of the drive shaft 44. Optional locking of the carrier 56 in the retracted position can be achieved by clockwise rotation of the plug 92.

(e) The plunger control knob 90 is rotated 180 degrees counter-clockwise to unlock the plunger 28 by placing the key 102 in engagement with the longitudinal groove 34 and out of registry with the radial groove 98, thereby allowing the plunger 28 to traverse the longitudinal axis of the syringe barrel 12 for normal operating use.

(f) After drawing a therapeutic composition into the dosage chamber 22 by pulling the plunger 28 proximally, and injecting the composition through the needle 66 by pushing the plunger 28 distally, the plunger 28 can then be locked again by 180 degree clockwise rotation of the plunger control knob 90, prohibiting it from traversing the axis of the syringe barrel 12, in preparation for propelling the carrier 56 forward for recoupling with the injection needle 66.

(g) The needle carrier 56 is once again propelled longitudinally forward, as explained under (a) and (b) above, through the plunger membrane 42 and recouples itself to the injection needle 66. Counter-clockwise rotation is required by the finger control knob 26 as explained under (c) above to unlock the needle 66 for retraction.

(h) Retraction of the needle 66 and carrier 56 coupled together also proceeds from subsequent counter-clockwise relative rotation of the drive shaft 44. Locking the carrier 56 in the retracted position can be achieved by clockwise rotation of the plug 92.

(i) The contaminated injection needle 66 is retracted within the syringe barrel 12 and the plunger 28, which serves as a sharps container thereafter, providing a means for safe handling and transport prior to discarding.

While the invention has been described in detail for the preferred form, it will be understood that modifications may be made without departure from the claimed scope of the invention.

What is claimed is:

1. A protractable and retractable hypodermic needle syringe device comprising:

a. a syringe barrel comprising a proximal end, a distal end, an outside surface, and an inside surface defining a dosage chamber and having a key laterally projecting from the inside surface into the dosage chamber;

b. a cylindrical plunger adapted for selective linear longitudinal movement within the syringe barrel between a dosage loading position wherein the plunger is moved toward the proximal end of the syringe barrel, and a dosage discharging position wherein the plunger is moved toward the distal end of the syringe barrel, comprising a cam sleeve having an outside surface defining a groove longitudinally extending along a portion of the sleeve and being complimentarily shaped to and in registry with the key, an inside surface having a helical cam groove longitudinally extending therealong, a proximal end, a distal end, and a resealable membrane positioned over the distal end;

c. a cylindrical cam drive shaft rotatably positioned within the cam sleeve, having a forward end, a rear end and a longitudinal cam slot therethrough;

d. a needle carrier movably positioned within the cam drive shaft comprising a body portion having a forward end, an opposite rear end, and a cam tab laterally projecting from the body portion in communication with both the longitudinal cam slot on the cam drive shaft and the helical groove on the cylindrical cam sleeve, the carrier being movable between a protracted position toward the distal end of the syringe barrel and a retracted position toward the proximal end of the barrel; and, e. a hypodermic needle detachably mounted on the forward end of the body portion, whereby rotating the cam drive shaft in a first direction engages the cam tab and rotates the needle carrier to its protracted position via the helical groove, resulting in the needle penetrating the resealable membrane to move to an operable position, and whereby rotating the cam drive shaft in an opposite second direction engages the cam tab and rotates the needle carrier to its retracted position.

2. The device of claim 1, further comprising a sealing means between the needle and the syringe barrel when in the operable position.

3. The device of claim 2, wherein the sealing means comprises an annular rib extending circumferentially about the needle and an annular indentation on the distal end of the interior surface of the syringe barrel in mating engagement with the rib when in the operable position.

4. The device of claim 1, further comprising a means for selectively retaining the needle in the operable position.

5. The device of claim 4, wherein the retaining means is a locking tab extending from the body portion of the needle in rotatable communication when in the operable position with a corresponding notch adjacent the distal end of the syringe barrel.

6. The device of claim 1, wherein the longitudinal cam slot has opposed ends that terminate in oppositely directed stop slots.

7. The device of claim 1, further comprising a finger support adjacent the proximal end of the syringe barrel comprising a pair of laterally extending finger flanges providing a position for engagement by the index finger and middle finger of the user while moving the plunger distally into the dosage discharging position.

8. The device of claim 1, further comprising a means for selectively releasing the needle when in the operable position.

9. The device of claim 8, wherein the releasing means is a finger control knob positioned adjacent the proximal end of the syringe barrel having a cylindrical body portion extending about the proximal end of the syringe barrel and a key laterally extending from the inside surface corresponding to and in rotatable communication with the longitudinal groove on the cam sleeve, and thereby and the needle carrier, between a release position wherein the forward end of the needle carrier releases the needle in the operative position, and a retaining position wherein the forward end of the needle carrier retains the needle.

10. The device of claim 1, further comprising a means for selectively locking the needle carrier in the retracted position.

11. The device of claim 10, wherein the locking means comprises the rear end of the needle carrier defining an opening into the body portion and a plug having a forward portion which is detachably mounted in the opening in the rear end of the needle carrier, and a rear portion which extends through the rear end of the drive shaft, and having a diameter which is greater that the diameter of the drive shaft, rotatable between a locked position wherein the forward portion of the plug retains the needle carrier in the retracted position, and an unlocked position wherein the forward portion of the plug releases the needle carrier.

12. The device of claim 1, further comprising a means for selectively preventing the plunger from longitudinal movement.

13. The device of claim 12, wherein the preventing means is a groove radially extending from the longitudinally extending groove on the cam sleeve and being located adjacent the proximal end of the cam sleeve, and a plunger control knob adjacent and external to the proximal end of the syringe barrel having a cylindrical body portion extending about the proximal end of the syringe barrel and a key laterally extending from the inside surface, and being rotatable between a locked position wherein the key is in engagement with the radial groove and out of registry with the longitudinal groove on the outside surface of the cam sleeve preventing the plunger from moving longitudinally within the syringe barrel, and an unlocked position wherein the key is in engagement with the longitudinal groove and out of registry with the radial groove permitting the plunger to move longitudinally within the syringe barrel.

* * * * *